United States Patent

Manna et al.

(10) Patent No.: US 7,776,027 B2
(45) Date of Patent: Aug. 17, 2010

(54) MEDICAL HANDPIECE WITH AUTOMATIC POWER SWITCHING MEANS

(75) Inventors: Ronald R. Manna, Valley Stream, NY (US); Scott Isola, Deer Park, NY (US); Theodore A. D. Novak, King Park, NY (US)

(73) Assignee: Misonix, Incorporated, Farmingdale, NY (US)

( * ) Notice: Subject to any disclaimer, the term of this patent is extended or adjusted under 35 U.S.C. 154(b) by 1030 days.

(21) Appl. No.: 10/194,819

(22) Filed: Jul. 11, 2002

(65) Prior Publication Data

US 2004/0010250 A1 Jan. 15, 2004

(51) Int. Cl.
*A61B 18/14* (2006.01)
(52) U.S. Cl. ...................... 604/540; 606/169
(58) Field of Classification Search .............. 604/31, 604/22, 540–543, 902; 606/169, 42
See application file for complete search history.

(56) References Cited

U.S. PATENT DOCUMENTS

| | | | | |
|---|---|---|---|---|
| 1,675,131 A * | 6/1928 | Phelan et al. | ............... | 200/229 |
| 2,056,377 A * | 10/1936 | Wappler | .................. | 606/48 |
| 2,203,061 A * | 6/1940 | Schmettow | ............. | 200/61.48 |
| 2,852,634 A | 9/1958 | Garland | | |
| 3,589,363 A * | 6/1971 | Banko et al. | ................. | 604/22 |
| 3,995,131 A | 11/1976 | Long | | |
| 4,043,342 A * | 8/1977 | Morrison, Jr. | ................. | 606/48 |
| 4,057,701 A | 11/1977 | Sisk et al. | | |
| 4,063,557 A * | 12/1977 | Wuchinich et al. | ............. | 604/22 |
| 4,418,692 A * | 12/1983 | Guay | .......................... | 606/42 |
| 4,492,832 A | 1/1985 | Taylor | | |
| 4,979,952 A * | 12/1990 | Kubota et al. | ................ | 606/169 |
| 5,026,387 A * | 6/1991 | Thomas | ....................... | 606/169 |
| 5,123,903 A | 6/1992 | Quaid et al. | | |
| 5,149,926 A * | 9/1992 | Ono | ..................... | 200/61.45 M |
| 5,160,317 A * | 11/1992 | Costin | .......................... | 604/22 |
| 5,178,012 A * | 1/1993 | Culp | ............................ | 73/510 |
| 5,201,373 A * | 4/1993 | Bloechle | ...................... | 173/109 |
| 5,273,027 A * | 12/1993 | Sekino et al. | .................. | 601/54 |
| 5,344,420 A * | 9/1994 | Hilal et al. | ..................... | 606/28 |
| 5,345,824 A * | 9/1994 | Sherman et al. | ........... | 73/514.18 |
| 5,419,761 A | 5/1995 | Narayanan et al. | | |
| 5,449,370 A * | 9/1995 | Vaitekunas | ................... | 606/169 |
| 5,472,447 A * | 12/1995 | Abrams et al. | .............. | 606/169 |
| 5,514,086 A * | 5/1996 | Parisi et al. | .................... | 604/22 |
| 5,599,347 A * | 2/1997 | Hart et al. | ...................... | 606/42 |
| 5,674,235 A | 10/1997 | Parisi | | |

(Continued)

*Primary Examiner*—Tatyana Zalukaeva
*Assistant Examiner*—Paula L Craig
(74) *Attorney, Agent, or Firm*—R. Neil Sudol; Henry D. Coleman; William J. Sapone

(57) ABSTRACT

A medical instrument includes a handpiece, an electromechanical transducer disposed in the handpiece, and an electrical circuit disposed at least partially in the handpiece for supplying alternating electrical current of a predetermined frequency to the transducer. A probe is operatively connected to the transducer for transmitting vibrations generated by the transducer to an operative site in a patient. A switching device is mounted to the handpiece and is operatively connected to the circuit and the transducer for enabling the supply of power to the transducer during a motion of the probe in a preselected direction relative to the handpiece and for disabling the supply of power to the transducer upon a termination of motion of the probe in the preselected direction.

13 Claims, 4 Drawing Sheets

U.S. PATENT DOCUMENTS

| | | | |
|---|---|---|---|
| 5,704,435 A * | 1/1998 | Meyer et al. | 173/176 |
| 5,712,543 A * | 1/1998 | Sjostrom | 318/71 |
| 5,728,130 A * | 3/1998 | Ishikawa et al. | 606/185 |
| 5,769,211 A * | 6/1998 | Manna et al. | 200/549 |
| 5,935,142 A * | 8/1999 | Hood | 606/169 |
| 5,968,060 A * | 10/1999 | Kellogg | 606/169 |
| 5,997,533 A * | 12/1999 | Kuhns | 606/41 |
| 6,013,048 A * | 1/2000 | Podany et al. | 604/22 |
| 6,053,906 A * | 4/2000 | Honda et al. | 606/1 |
| 6,352,532 B1 * | 3/2002 | Kramer et al. | 606/41 |
| 6,494,095 B1 * | 12/2002 | Wan | 73/514.26 |
| 7,476,233 B1 * | 1/2009 | Wiener et al. | 606/169 |
| 2003/0040737 A1 * | 2/2003 | Merril et al. | 606/1 |
| 2004/0230262 A1 * | 11/2004 | Sartor et al. | 607/96 |
| 2006/0058783 A1 * | 3/2006 | Buchman | 606/42 |

\* cited by examiner

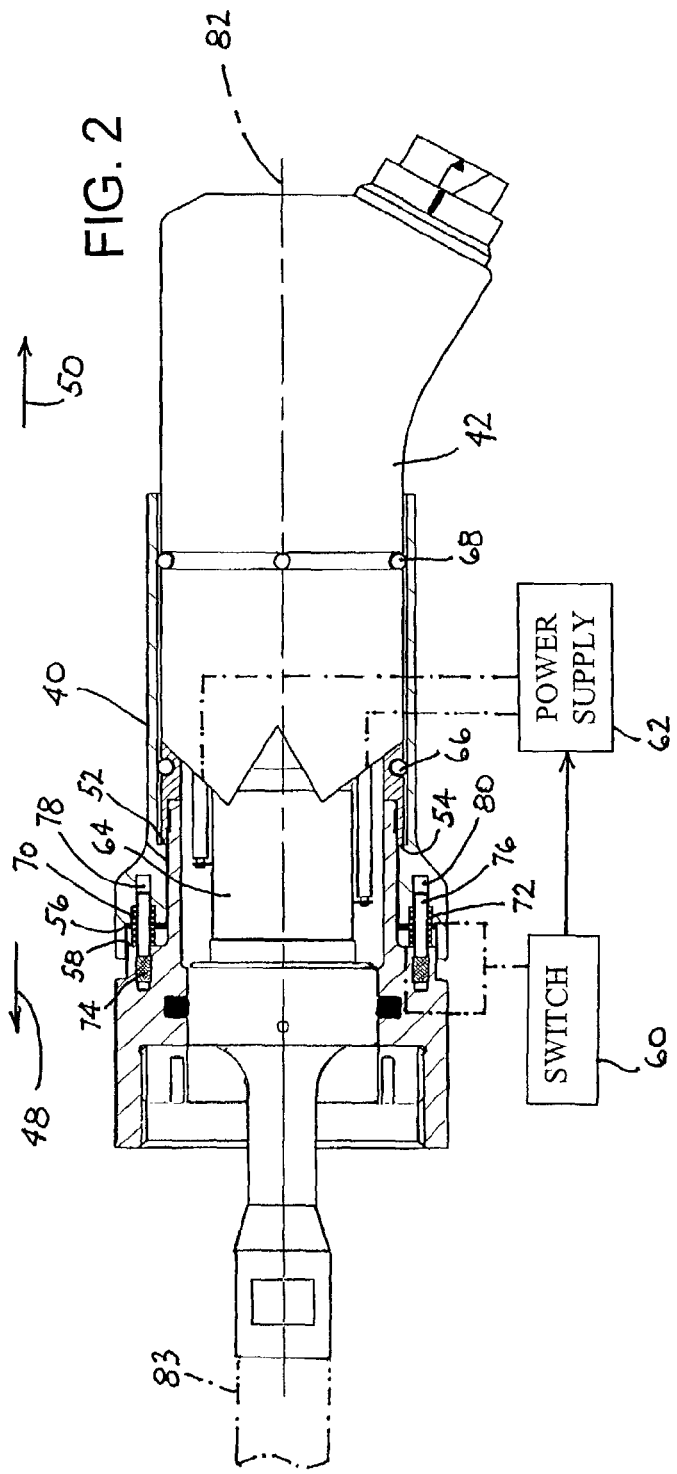
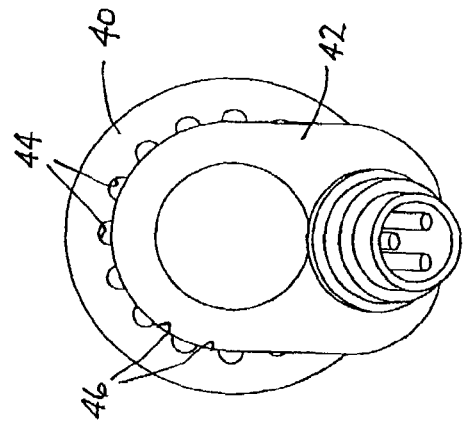

MEDICAL HANDPIECE WITH AUTOMATIC POWER SWITCHING MEANS

BACKGROUND OF THE INVENTION

This invention relates to a medical instrument and to an associated method. More particularly, this invention relates to a medical instrument and method wherein power to an operative tip is automatically controlled.

Ultrasonic devices have been used to remove soft and hard tissue from mammalian bodies for over three decades, at least. These devices and methods for their use have been well documented in the art, such as U.S. Pat. No. 4,223,676 to Wuchinich, U.S. Pat. No. 4,827,911 to Broadwin and U.S. Pat. No. 5,419,761 to Narayanan et al. Applications include phacoemulsification, ablation of tumors in the liver and spine and subcutaneous removal of adipose tissue, also known as ultrasonic liposuction.

Most of the instruments used for these applications have several elements in common. These are an electrical generator which transforms line or battery power to relatively high voltage RF frequencies in the 20 kc to 100 kc range, a transducer of either a magnetostrictive or piezoelectric type and a probe or horn which is generally manufactured from titanium and amplifies the motion of the transducer from approximately 20 microns to over 400 microns in some cases. Means have been disclosed which allow the surgeon the ability to switch the output power on or off on demand. These include footswitch controls, finger or thumb switches on the handpiece or even by voice commands if the electronic generator includes the prerequisite software and electronics.

All of these means require that the surgeon coordinate the application or removal of ultrasonic power to the precise moment at which it is required. In spinal or brain surgery, this is not difficult, since the application of the power is not continuous and he or she has complete view of the operative site. By simply moving his hand, he is able to apply power to the surgical site and remove the tip of the probe even when the power is on, limiting the power input to tissue. In this way, tissue temperature rise is minimized and collateral damage is curtailed.

However, in applications such as liposuction, the surgeon would have a difficult time in controlling power requirements. In this case, the surgeon moves the handpiece with a piston like action, alternatively advancing and retracting the cannula in a predetermined pattern. See U.S. Pat. No. 5,527,273 for a more complete description of this action. Since the sides of the long cannula are in contact with the tissue at all times, power is being applied to the tissue as long as the probe is activated with ultrasonic energy. In actuality, the power is only required on the pushing stroke, since the ultrasonic power ablates the tissue in direct contact with the distal end of the probe. As the tissue disrupts, it liquefies and the cannula can be advance. In this way, channels or tunnels are created in the adipose tissue.

When the probe is pulled back to be repositioned and start another tunnel, the tissue contacts the side of the probe. Power is still being applied but tissue liquefaction does not occur, since it is the cavitation and shearing forces created by the probe tip that liquefies and emulsifies the cells. Therefore, this energy can be considered waste and it actually goes into tissue heating. The longer the probe is used, the higher the temperature rise will be. If the temperature rises above the necrosis point, burning, scarring and other deleterious effects will arise.

It would be difficult and tiring for the surgeon to time the on and off controls with his hand movements, since they are rapid and repetitive. It would be more desirable to have an automatic means to determine the power requirement and have the machine apply energy only when most needed.

Several embodiments for reducing the amount of ultrasonic power delivered to the tissue or samples have been known to the art for many years. One old technique is pulsing of the output. By automatically turning the output power on and off at specific duty cycles, the power may be reduced in inverse proportion to the output duty cycle. For instance, if the output power was turned on for $2/10$ths of a second and shut off for the remainder of that second, it would be said the output power had a 20% duty cycle. At the beginning of the next second, the power is turned back on for $2/10$ths of a second and so forth. The power input to the tissue or sample would be reduced by 80% over a given period. However, this embodiment does not turn off the power completely when not needed, i.e. on the return stroke, it only lessens it. In fact, the power is even reduced on the push stroke, when it is most needed increasing the effort needed to advance the cannula through the body.

OBJECTS OF THE INVENTION

An object of the present invention is to provide a medical instrument and/or an associated method wherein the control of power transmission to an operative tip is facilitated.

Another object of the present invention is to provide such a medical instrument and/or an associated method wherein power transmission to the operative tip is effectuated automatically, without requiring any dedicated separate action on the part of the surgeon.

A related object of the present invention is to provide a liposuction instrument and/or an associated surgical method for reducing, if not minimizing, trauma to tissues of a patient.

Yet another object of the present invention is to provide an ultrasonic liposuction instrument that is easier to use than conventional ultrasonic liposuction probes.

These and other objects of the present invention will be apparent from the drawings and descriptions herein. Although every object of the invention is attained by at least one embodiment of the invention, there is not necessarily any embodiment in which all of the objects are met.

SUMMARY OF THE INVENTION

The present invention is directed in part to a medical instrument and an associated method wherein power is automatically delivered to an operative tip only when the instrument is being advanced through tissues of a patient. Energy or power is automatically turned off when the instrument and particularly the operative tip is no longer being advanced, for instance, is being retracted.

A medical instrument in accordance with the present invention comprises a handpiece, an electromechanical transducer disposed in the handpiece, an electrical circuit disposed at least partially in the handpiece for supplying alternating electrical current of a predetermined frequency to the transducer, a probe operatively connected to the transducer for transmitting vibrations generated by the transducer to an operative site in a patient, and a switching device mounted to the handpiece and operatively connected to the circuit and the transducer for enabling the supply of power to the transducer during a motion of the probe in a preselected direction relative to the handpiece and for disabling the supply of power to the transducer upon a termination of motion of the probe in the preselected direction.

The handpiece may include a main body portion and a grip portion movably coupled to one another. In that case, the switching device including two electrical contacts respectively mounted to the main body portion and the grip portion, the switching device further including a spring carried by the handpiece for biasing the main body portion and the grip portion relative to one another.

Typically, the spring is a compression spring disposed between the body portion and the grip portion of the handpiece for biasing them away from one another to thereby maintain the electrical contacts spaced from one another. In this embodiment, the handpiece has a distal end and a proximal end, the probe extending from the distal end of the handpiece, while the preselected direction is a distal or forward direction. The grip portion is located proximally of the main body portion. Upon a manual pushing of the handpiece via the grip portion, the frictional contact of the probe with the tissues of the patient reduces the forward motion of the body portion relative to the motion of the grip portion, so that the electrical contacts engage and enable a current flow to the transducer.

In a particularly useful embodiment of the invention, the probe is elongate, the predetermined frequency is an ultrasonic frequency, and the instrument is an ultrasonic liposuction instrument.

In accordance with an alternative feature of the invention, the switching device is an inertial mass switch or a load sensor.

Another embodiment of a medical instrument in accordance with the present invention comprises a handpiece, an operative tip connected to the handpiece, and transmission means mounted at least in part to the handpiece and operatively coupled to the operative tip for supplying power to the operative tip, whereby the operative tip is enabled to effectuate a predetermined kind of surgical operation on a patient. This embodiment additionally comprises a motion sensor mounted to the handpiece and operatively connected to the transmission means for enabling the transmission means to supply power to the operative tip only during motion of the operative tip in a preselected direction defined relative to the handpiece.

The motion sensor may be a spring-loaded switch. Where the handpiece includes a main body portion and a grip portion movably coupled to one another, the switch includes two electrical contacts respectively mounted to the main body portion and the grip portion and further includes a spring carried by the handpiece for biasing the main body portion and the grip portion relative to one another.

Alternatively, the motion sensor may be an inertial-mass-type sensor or a load sensor.

A method for performing a surgical operation utilizes, in accordance with the present invention, a medical instrument having a handgrip at a proximal end and an operative tip at a distal or free end. The method comprises (1) moving the medical instrument in a preselected direction relative to the medical instrument, (2) by virtue of the moving of the medical instrument in the preselected direction, automatically transmitting power to the operative tip during the moving of the medical instrument in the preselected direction, (3) terminating the motion of the medical instrument in the preselected direction, and (4) by virtue of the terminating of the motion of the medical instrument, automatically terminating the transmission of power to the operative tip.

The medical instrument may be provided with a motion sensor. In that event, the automatic transmitting of power to the operative tip includes operating the sensor to detect motion of the medical instrument in the preselected direction, whereas the automatic terminating of the power transmission to the operative tip includes operating the sensor to detect a cessation of motion in the preselected direction.

Pursuant to another feature of the present invention, the method further comprises transmitting power to the operative tip only when the medical instrument is being moved in the preselected direction. More specifically, the method comprises transmitting power to the operative tip only when the medical instrument is being moved in the preselected direction through a mass providing frictional resistance to passage of the instrument.

In a medical instrument in accordance with the present invention, the control of power transmission to an operative tip is facilitated by being made dependent on the motion of the instrument through the organic tissues of the patient. The turning of power alternately on and off is achieved automatically without the surgeon having to operate any control. The surgeon merely moves the instrument in the desired direction and back again.

A medical instrument in accordance with the present invention reduces trauma to tissues of a patient, for example, in ultrasonically assisted liposuction.

BRIEF DESCRIPTION OF THE DRAWINGS

FIG. 2 is a partial longitudinal cross-section view of another embodiment of a handpiece for an ultrasonic liposuction instrument, showing another spring-loaded handgrip containing a motion-actuated power control switch, in accordance with the present invention.

FIG. 3 is an end elevational view of the handpiece of FIG. 2.

DEFINITIONS

The term "medical instrument" is used herein to denote any device that is used in contact with organic tissues of a patient to perform a diagnostic or therapeutic procedure.

The term "operative tip" as used herein designates a portion of a medical instrument that is placed into contact with organic tissues of a patient during a medical procedure. Typically, the operative tip is functional to effect a surgical operation on organic tissues. For instance, an operative tip may be a free end of an ultrasonically vibrating probe or cannula. Alternatively, an operative tip may be a cauterization element of an electrocautery applicator, a scissors, a vibrating scalpel, a suction port, an irrigation port, etc.

The word "handpiece" as used herein relates to a casing, frame, holder, or support which can be manually carried and manipulated during a medical operation on a patient.

A "power-transmission circuit" or "circuit" as that term is used herein means any hardware used to move energy from a source to a load. The power transmitted may be mechanical, electrical, magnetic, hydraulic, or pneumatic. The hardware may include mechanical structural elements, transducers, electrical circuits, electrical leads, magnetic materials, and hydraulic or pneumatic conduits and valves. The hardware may additionally include power sources: voltage or current sources, magnets, pressurized or pressurizable reservoirs of fluid of air.

The term "switching device" is used herein to generally describe any manually operable control utilizable in conjunction with a power-transmission circuit for alternately enabling and disabling the flow of power through the circuit. A switch may be mechanical, electrical, electromagnetic, magnetic, hydraulic, or pneumatic. Specific examples include spring-loaded electrical contact switches, gravity or inertial switches, and load switches.

A "motion sensor" as that term is used herein refers to any detector device responsive to a velocity or acceleration. A motion sensor may be mechanical or electromechanical as in the case of a micro-switch functioning in the manner of a hair sensor. A motion sensor may take the form of a gravity switch or an inertial switch or a mercury switch. A motion sensor may be a load sensor such as a stack of piezoelectric crystals sensing compression due to a resistance to motion.

DETAILED DESCRIPTION OF THE PREFERRED EMBODIMENTS

Together with improvements disclosed herein, the drawings show sections of a medial instrument handpiece disclosed in U.S. Pat. No. 5,769,211, the disclosure of which is hereby incorporated by reference.

Figure 1:
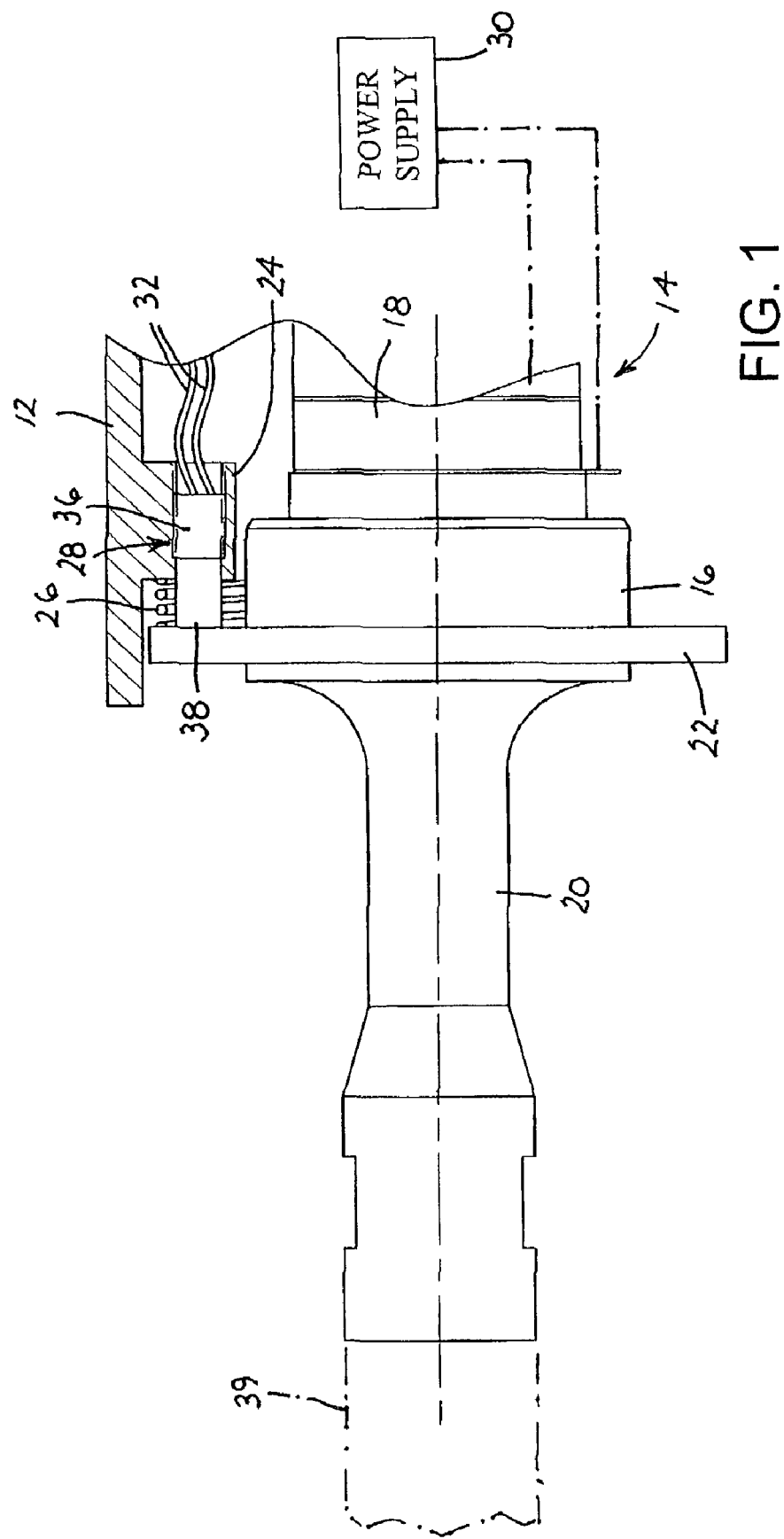
FIG. 1 is a partial longitudinal cross-section view of a handpiece for an ultrasonic liposuction instrument, showing a spring-loaded handgrip containing a motion-actuated power control switch, in accordance with the present invention.

As illustrated in FIG. 1, an ultrasonic handpiece comprises a handgrip portion in the form of a sleeve 12 that surrounds and is movably mounted to a transducer array 14. Transducer array 14 includes a front driver 16 and a stack of piezoelectric crystals 18. Front driver 16 is coupled to an ultrasonic horn 20 that amplifies ultrasonic pressure waves produced by the stack of crystals 18. Front driver 16 is provided at a vibration node with an outwardly extending circumferential flange 22, while sleeve 12 is provided with an inwardly extending circumferential flange (or a plurality of angularly spaced inwardly extending projections) 24. A helical compression spring 26 surrounds front driver 16 and is sandwiched between flanges 22 and 24. Compression spring 26 biases flanges 22 and 24 away from one another.

Flange 24 carries a switch 28 that is connected to an electrical a-c power supply 30 via a pair of leads 32. Switch 28 controls the transmission of an ultrasonic-frequency electrical waveform from supply 30 to transducer array 14. Switch 28 includes a switch body 36 provided with an actuator 38 such as a telescoping plunger element. Switch actuator 38 is attached directly to flange 22 and or indirectly to flange 24 via switch body 36.

As disclosed more fully hereinbelow with reference to FIGS. 2 and 3, sleeve or handgrip 12 is shiftably mounted to a casing or housing (not shown in FIG. 1) and has a length determined from ergonomic studies of the average width of surgeons' hands. The spring 26 provides enough force to maintain actuator 38 extended from switch body 36 so that internal switch contacts (not shown) are separated when the instrument is at rest. A surgeon grasps the handpiece around the sleeve 12 and provides force by pushing the cannula or probe 39 into the target tissues of the patient. Spring 26 is compressed by that force so that the electrical internal contacts of switch 28 close, transmitting electrical power to transducer array 14 as previously disclosed. As long as sufficient resistance exists against the forward movement of the handpiece and cannula 39, the switch will remain closed and the output energy will be on.

As the surgeon begins to extract the instrument from the patient, the force on the distal end of the cannula or probe 39 is relieved. Spring 26 pushes the actuator 38 out of switch body 36 thereby separating the internal switch contacts turning the power off. As the surgeon continues to retract the handpiece, the switch 28 remains open, thereby eliminating power input to the site for the entire time the cannula 39 is moving backwards. Tissue temperature cannot rise during the retraction phase and in fact lowers since energy input during ultrasound activation is allowed to conduct away. If the spring 26 has a sufficiently great spring constant, the switch contacts will remain apart even if the handpiece is at rest. Therefore, if the surgeon stops to rest or otherwise pauses the stroking action, the ultrasonic power will remain off until he repositions and advances the cannula 39 again.

FIGS. 2 and 3 show a handpiece like that of FIGS. 2A and 2B of U.S. Pat. No. 5,769,211 modified to provide an actuator sleeve 40 which surrounds a substantially cylindrical handle or handpiece case 42. Actuator sleeve 40 has an internal surface provided with a plurality of angularly equispaced grooves 44 which define a plurality of angularly equispaced ribs 46. Ribs 44 have an internal diameter which is slightly greater than the outside diameter of handpiece case 42 upon which the ribs ride. In this manner, a sliding fit is achieved which allows sleeve 40 to be translated alternately in a distal direction 48 and a proximal direction 50. A shoulder, ledge or abutment 52 on sleeve 40 is engageable with a shoulder 54 of case 42 to prevent sleeve 40 from being slid off the back of the case. Recesses or grooves 46 on the inner diameter of sleeve 40 reduce the amount of material in contact with handpiece case 42. This reduced contact decreases friction and prevents debris from collecting between sleeve 40 and handpiece case 42, which prevents the sleeve from sticking or binding.

Sleeve 40 has a distally directed surface (not designated) which is faced with an electrically conductive lining 56 which does not corrode in the presence of steam or detergents, such as stainless steel. This lining 56 is either glued or staked to sleeve 40, using methods known to the art. A mating face 58 is fashioned on handpiece case 42. This face 58 is manufactured from a material which is generally nonconductive, such as thermoplastics. A switch 60 has parts (see U.S. Pat. No. 5,769,211) provided along lining 56 and face 58, those parts closing the switch upon an approach of lining 56 and face 58. The closing of switch 60 conducts current from a power supply 62 to a transducer array or piezoelectric crystal stack 64.

Low friction bushings 66 and 68 or other such bearings are located on the handpiece body or case 42 and locate the sleeve so that it is essentially coaxial with the handpiece body itself.

In order to allow an automatic opening of switch 60 upon an interruption in forward motion of the instrument, owing to the surgeon's reduction in forward force on sleeve 40, sleeve 40 is spring loaded. As depicted in FIG. 2, two helical or coil springs 70 and 72 are placed between sleeve 40 and handpiece face 58. Coil springs 70 and 72 are spaced 90° from each contacts of switch 60 (see U.S. Pat. No. 5,769,211). Two pins 74 and 76 are pressed into handpiece face 58 and are thereby fixed in place. Pins 74 and 76 engage blind holes 78 and 80 drilled into sleeve 40, whereby the pins perform both a locating or mounting function for coil springs 70 and 72 and a keying junction for sleeve 40 to prevent the sleeve from rotating about a longitudinal axis 82 of handpiece case 42.

The coil springs 70 and 72 provide sufficient force to keep the contacts of switch 60 separated during rest. As the surgeon grasps the handpiece around the sleeve 40, he of she exerts a force in the distal direction, thereby pushing the cannula or probe 83 into the target tissues. Springs 70 and 72 are compressed by the applied force and the contacts of switch 60 close, turning the energy on as previously disclosed. As long as sufficient resistance exists against the forward movement of the handpiece and cannula 83, the switch 60 will remain closed and the output energy will be on.

As the surgeon begins to retract the instrument, the force on the distal end of the cannula or probe 83 is relieved. The springs 70 and 72 push the switch contacts apart and the output power is turned off. As the surgeon continues to retract the handpiece, the switch 60 remains open, thereby eliminating power input to the site for the entire time the cannula 83 is moving backwards. Tissue temperature cannot rise during the retraction phase and in fact lowers since energy input during ultrasound activation is allowed to conduct away. If the springs 70 and 72 have sufficient energy, the switch contacts will remain apart even if the handpiece is at rest. Therefore, if the surgeon stops to rest or otherwise pauses the stroking action, the ultrasonic power will remain off until he repositions and advances the cannula 83 again.

Figure 4:
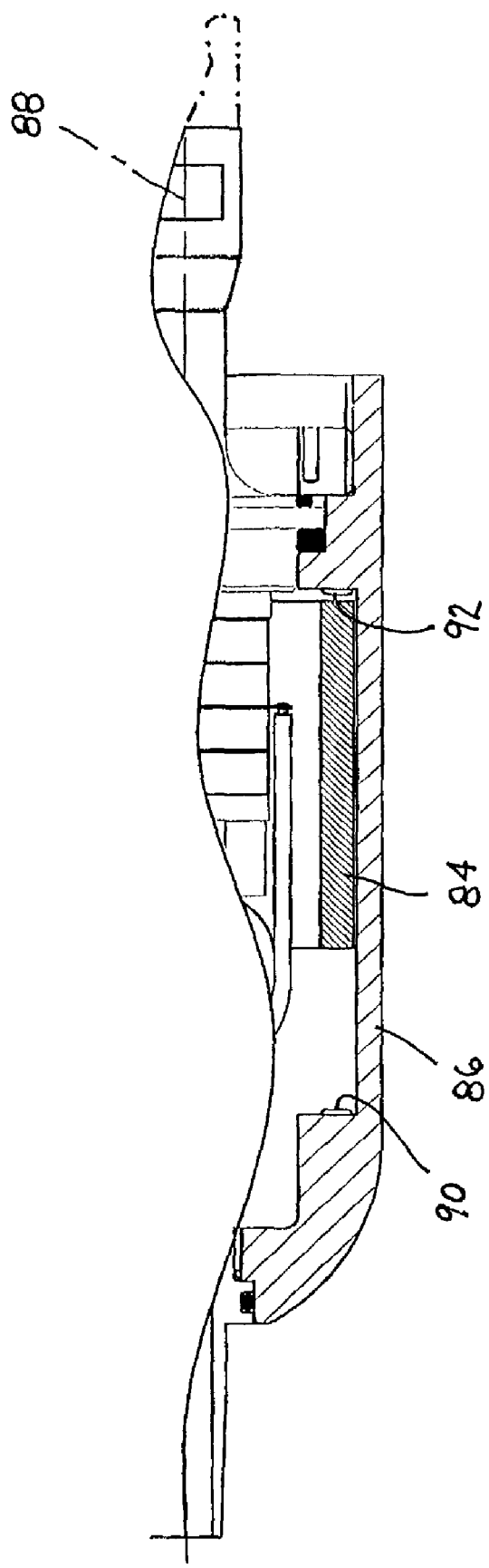
FIG. 4 is a partial longitudinal cross-sectional view of a further embodiment of a handpiece for an ultrasonic liposuction instrument, showing an inertial type motion-responsive power control switch, in accordance with the present invention.

Another embodiment, illustrated in FIG. 4, incorporates an inertial mass type switch. Here a relatively large mass 84 is suspended by a low friction bearing (not shown) inside a casing or housing 86 so that the mass can move parallel to a long axis 88 of the handpiece. As the handpiece is moved back and forth rapidly, the inertial mass 84 moves in the opposite direction as per Newton's laws of motion. As the mass 84 engages switch contacts 90 and 92 at either end of its travel path, the output of the ultrasound device may be turned on and off simultaneously. Preferably, the switching action occurs upon an initial engagement of the mass 84 with contacts 90 and 92. Light springs (not shown) can be used to center the mass 84 when at rest. The benefit of this is that the surgeon does not have to overcome force of a heavier spring to activate the output power. It is also useful when the resistance of the tissue or other load is slight.

Figure 5:
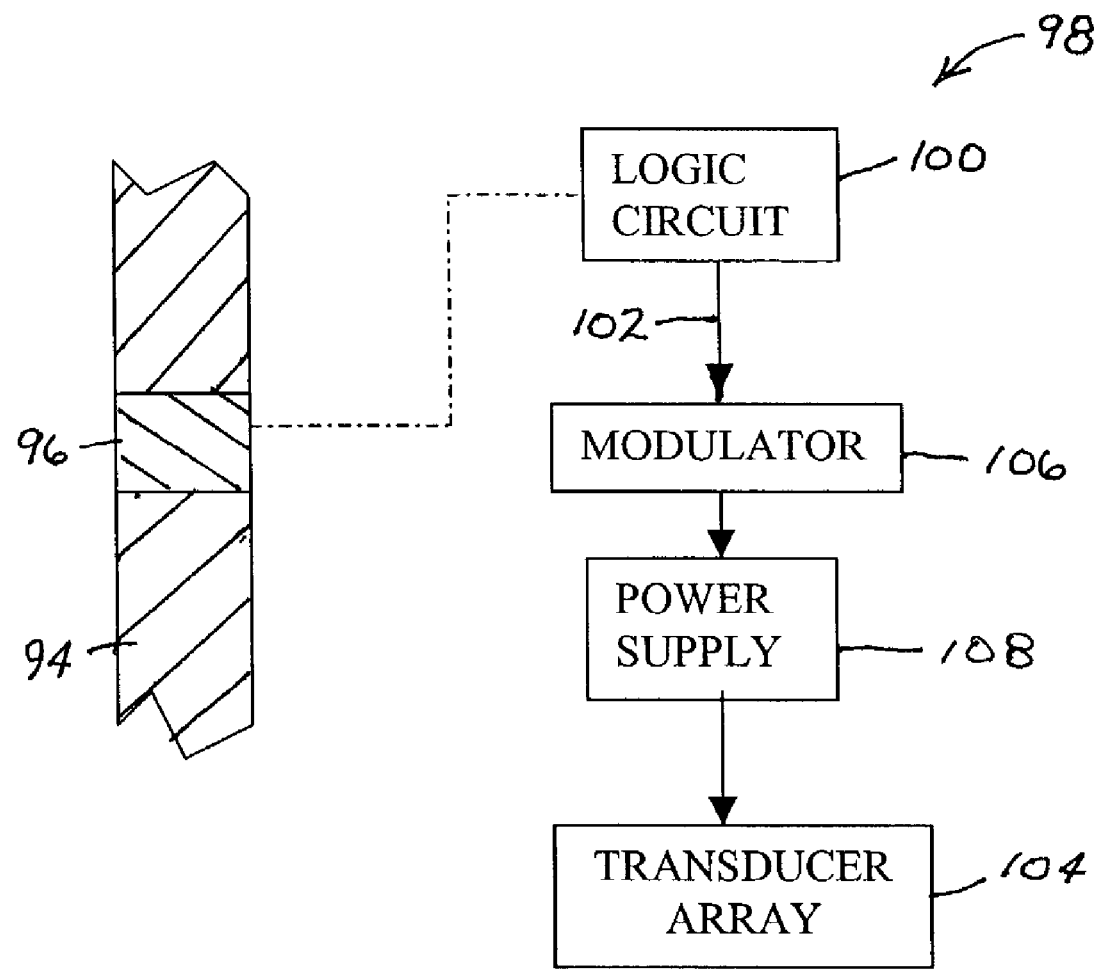
FIG. 5 is partially a block diagram and partially a schematic partial cross-sectional view of yet another handpiece for an ultrasonic liposuction instrument, showing a load-type motionsensitive power control switch, in accordance with the present invention.

In another embodiment, depicted diagrammatically in FIG. 5, a tubular handpiece casing 94 is connected to or incorporates a load-sensing device 96. This device could be a piezoelectric sensor, a strain gauge or other force or load-sensing element known to the art. Here, the level of force is measured. An electric switching circuit 98 incorporates logic or sensing circuits 100 that both measure the magnitude this force and provide an analog or digital signal 102 proportional to it. The output amplitude or energy from an ultrasonic transducer array 104 may be modulated by this signal, via a modulator 106 and a modulated power supply 108, to provide either a stepped on/off output or an output power level that is directly or inversely proportional to the applied force. FIG. 5 shows a simplified or schematic form of this embodiment. The electronic interface circuits required for this type of control are well known to the art.

Although the invention has been described in terms of particular embodiments and applications, one of ordinary skill in the art, in light of this teaching, can generate additional embodiments and modifications without departing from the spirit of or exceeding the scope of the claimed invention. For example, although the described surgical method describes a liposuction procedure done during plastic surgery, many other surgical procedures may benefit from this invention. Accordingly, it is to be understood that the drawings and descriptions herein are proffered by way of example to facilitate comprehension of the invention and should not be construed to limit the scope thereof.

What is claimed is:

1. A medical instrument comprising:
   a handpiece;
   an electromechanical transducer disposed in said handpiece;
   an electrical circuit disposed at least partially in said handpiece for supplying alternating electrical current of a predetermined frequency to said transducer;
   a probe operatively connected to said transducer for transmitting vibrations generated by said transducer to an operative site in a patient; and
   an at least partially automatic switching device mounted to said handpiece and operatively connected to said circuit and said transducer enabling the supply of power to said transducer during a motion of said probe in a preselected direction defined relative to said handpiece and automatically disabling the supply of power to said transducer upon a termination of motion of said probe in said preselected direction so that power is supplied to said transducer only when said probe is moving in said preselected direction.

2. The instrument defined in claim 1 wherein said handpiece includes a main body portion and a grip portion movably coupled to one another, said grip portion being sufficiently large to accommodate an entire adult hand, said switching device including two electrical contacts respectively mounted to said main body portion and said grip portion, said switching device further including a spring carried by said handpiece for biasing said main body portion and said grip portion relative to one another.

3. The instrument defined in claim 2 wherein said handpiece has a distal end and a proximal end, said probe extending from said distal end of said handpiece, said preselected direction being a distal or forward direction, said grip portion being located proximally of said main body portion, said spring being a compression spring disposed between said main body portion and said grip portion.

4. The instrument defined in claim 3 wherein said probe is elongate, said predetermined frequency is an ultrasonic frequency, and the instrument is an ultrasonic liposuction instrument.

5. The instrument defined in claim 2 wherein said grip portion is a sleeve surrounding said main body portion, said sleeve having a length parallel to an axis of said main body portion approximately equal to an average width of surgeons' hands.

6. The instrument defined in claim 1 wherein said handpiece has a distal end and a proximal end, said probe extending from said distal end of said handpiece, said preselected direction being a distal or forward direction.

7. The instrument defined in claim 1 wherein said predetermined frequency is an ultrasonic frequency and the instrument is an ultrasonic medical instrument.

8. The instrument defined in claim 1 wherein said switching device includes means for disabling the supply of power to said transducer solely in response to termination of motion of said probe in said preselected direction.

9. A medical instrument comprising:
   a handpiece;
   an electromechanical transducer disposed in said handpiece;
   an electrical circuit disposed at least partially in said handpiece for supplying alternating electrical current of a predetermined frequency to said transducer;
   a probe operatively connected to said transducer for transmitting vibrations generated by said transducer to an operative site in a patient; and an at least partially automatic switching device mounted to said handpiece and operatively connected to said circuit and said transducer for enabling the supply of power to said transducer during a motion of said probe in a preselected direction defined relative to said handpiece and for automatically disabling the supply of power to said transducer upon a termination of motion of said probe in said preselected direction, wherein said switching device is an inertial mass switch.

10. The instrument defined in claim 9 wherein said inertial mass switch includes a mass suspended in said main body portion so that said mass can move along a travel path parallel to an axis of said main body portion and relative to said main body portion.

11. The instrument defined in claim 9 wherein said switching device further includes means operatively connected to a load sensor for modulating an output of said electrical circuit in accordance with a level of force detected by said load sensor.

12. A medical instrument comprising:

a handpiece;

an electromechanical transducer disposed in said handpiece;

an electrical circuit disposed at least partially in said handpiece for supplying alternating electrical current of a predetermined frequency to said transducer;

a probe operatively connected to said transducer for transmitting vibrations generated by said transducer to an operative site in a patient; and an at least partially automatic switching device mounted to said handpiece and operatively connected to said circuit and said transducer enabling the supply of power to said transducer during a motion of said probe in a preselected direction defined relative to said handpiece and automatically disabling the supply of power to said transducer upon a termination of motion of said probe in said preselected direction so that power is supplied to said transducer only when said probe is moving in said preselected direction, wherein said switching device includes an electromechanical load sensor.

13. A medical instrument comprising:

a handpiece;

an electromechanical transducer disposed in said handpiece;

an electrical circuit disposed at least partially in said handpiece for supplying alternating electrical current of a predetermined frequency to said transducer;

a probe operatively connected to said transducer for transmitting vibrations generated by said transducer to an operative site in a patient; and an at least partially automatic switching device mounted to said handpiece and operatively connected to said circuit and said transducer for enabling the supply of power to said transducer during a motion of said probe in a preselected direction defined relative to said handpiece and for automatically disabling the supply of power to said transducer upon a termination of motion of said probe in said preselected direction, wherein said handpiece includes a main body portion and a handgrip movably attached to said main body portion, said probe being stationary or fixed with respect to said main body portion of said handpiece, and said switching device including electrical contacts mounted to said main body portion and said handgrip, said electrical contacts being operatively connected to said circuit and said transducer for enabling the supply of power to said transducer during a motion of said probe in a preselected direction defined relative to said handpiece and for automatically disabling the supply of power to said transducer upon a termination of motion of said probe in said preselected direction.

* * * * *